United States Patent
Mojahedi et al.

(10) Patent No.: US 10,190,981 B2
(45) Date of Patent: Jan. 29, 2019

(54) MULTIMODE SPECTROSCOPY APPARATUSES AND METHODS

(71) Applicant: THE GOVERNING COUNCIL OF THE UNIVERSITY OF TORONTO, Toronto (CA)

(72) Inventors: Mohammad Mojahedi, Oakville (CA); Farshid Bahrami, North York (CA); James Stewart Aitchison, Toronto (CA)

(73) Assignee: THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 0 days.

(21) Appl. No.: 15/309,639

(22) PCT Filed: May 8, 2015

(86) PCT No.: PCT/CA2015/000300
§ 371 (c)(1),
(2) Date: Nov. 8, 2016

(87) PCT Pub. No.: WO2015/168776
PCT Pub. Date: Nov. 12, 2015

(65) Prior Publication Data
US 2017/0268995 A1 Sep. 21, 2017

Related U.S. Application Data

(60) Provisional application No. 61/990,272, filed on May 8, 2014.

(51) Int. Cl.
*G01N 21/55* (2014.01)
*G01N 21/552* (2014.01)

(52) U.S. Cl.
CPC ......... *G01N 21/554* (2013.01); *G01N 21/553* (2013.01); *G01N 2201/12* (2013.01)

(58) Field of Classification Search
CPC ..... G01B 11/18; G01N 21/553; G01N 21/774
(Continued)

(56) References Cited

U.S. PATENT DOCUMENTS 6,330,387 B1 * 12/2001 Salamon ............... G01N 21/553
385/11
6,483,959 B1 * 11/2002 Singh .................. G01N 21/0303
385/12

(Continued)

FOREIGN PATENT DOCUMENTS

WO 2000058715 A2 10/2000
WO 2005040760 A1 5/2005
WO 2011006250 A1 1/2011

OTHER PUBLICATIONS

WIPO, International Search Report and Written Report for PCT Application No. PCT/CA2015/000300 dated Jul. 22, 2015.
(Continued)

*Primary Examiner* — Hoa Pham
(74) *Attorney, Agent, or Firm* — Norton Rose Fulbright Canada LLP (57) ABSTRACT

Apparatuses and methods for spectroscopy using multiple resonance modes are provided. Multiple resonance modes may be used for bulk sensing and/or surface sensing applications. A plasmon waveguide resonance sensor is provided for multimode spectroscopy. The sensor includes a dielectric layer; and a metallic layer coupled to the dielectric layer. The sensor is configured to provide: a first resonance mode for bulk sensing, in response to light of a given wavelength; and a second resonance mode for surface sensing, in response to light of the given wavelength. The first and second resonance modes have different polarizations. Surface plasmon
(Continued)

resonance assemblies are provided having a grating coupled to a surface plasmon resonance sensor, the grating being a dielectric grating or a metallic grating. The grating, in response to light, provides various resonance modes having at least two different polarizations for bulk and surface sensing.

5 Claims, 9 Drawing Sheets

(58) Field of Classification Search
USPC ............ 356/445–448, 451, 496, 517; 385/12
See application file for complete search history.

(56) References Cited

U.S. PATENT DOCUMENTS

| | | | | |
|---|---|---|---|---|
| 2006/0062509 | A1* | 3/2006 | Krol | G01N 21/552 |
| | | | | 385/12 |
| 2007/0139646 | A1* | 6/2007 | Singh | G01N 21/553 |
| | | | | 356/237.2 |
| 2011/0001975 | A1* | 1/2011 | Razansky | G01J 5/08 |
| | | | | 356/445 |

OTHER PUBLICATIONS

Bahrami, F., "Multimode spectroscopy in dielectric-grating-coupled surface plasmon sensors," Photonics Conference (IPC), 2013 IEEE, pp. 8-9, Sep. 8-12, 2013.
Alam, M.Z. et al, "Compact low loss and broadband hybrid plasmonic directional coupler," Optics Express, 21(13), pp. 16029-16034, Jun. 27, 2013, Optics Society of America.

* cited by examiner

MULTIMODE SPECTROSCOPY APPARATUSES AND METHODS

FIELD

This disclosure relates generally to spectroscopy, and more particularly to apparatuses and methods for multimode spectroscopy, including at a single wavelength.

BACKGROUND

Several optical methods have been used over the past decades to investigate thin biomolecular films. Surface plasmon resonance (SPR) spectroscopy is a well-established optical technique commonly used for this purpose.

Surface plasmon resonance (SPR) has gained interest as an efficient mechanism for biosensing. SPR biosensors are sensitive to the refractive index variations occurring within the penetration depth of their evanescent fields. Therefore, an SPR wave is not only sensitive to the variations of the refractive index within a few nanometers of a biomaterial layer on the metal surface (called the adlayer), but also to the variations in the index of the fluid above the adlayer. This cross sensitivity is more pronounced in affinity biosensors where studying the adlayer properties is of particular interest. In general, the aforementioned interfering effects can be attributed to the: adlayer refractive index ($n_a$), adlayer thickness ($d_a$), and bulk refractive index ($n_b$).

SPR sensors have high sensitivity due to their large field intensity at metal/dielectric interface. Any variations within the penetration depth of the wave can change its propagation constant which results in change in the output signal.

A combination of high sensitivity, label-free detection, and real time sensing make the SPR biosensors the preferred approach for many sensing applications. SPR sensing has been investigated in a variety of sensing configurations such as attenuated total reflection (ATR), grating couplers, optical waveguides, and optical fibers. Among these techniques, ATR using prism coupling is one of the most widely used optical excitation methods in the SPR community.

However, spectroscopy using an SPR wave cannot distinguish between variations in more than one parameter within the penetration depth.

Accordingly, improved apparatuses and methods for performing spectroscopy, or at least alternative, are desirable.

SUMMARY

In an aspect, a plasmon waveguide resonance sensor for multimode spectroscopy is provided. The sensor includes a dielectric layer; and a metallic layer coupled to the dielectric layer, and configured to provide: a first resonance mode for bulk sensing, in response to light of a given wavelength; and a second resonance mode for surface sensing, in response to light of the given wavelength. The first and second resonance modes have different polarizations.

In another aspect, the first resonance mode is a transverse magnetic mode.

In another aspect, the second resonance mode is a transverse electric mode.

In another aspect, the sensor further comprises a prism through which the light passes.

In another aspect, the sensor is configured in a Kretschmann configuration.

In another aspect, a method of performing multimode spectroscopy is provided. The method includes providing a plasmon waveguide resonance sensor; providing light of a given wavelength to the plasmon waveguide resonance sensor; and operating the plasmon waveguide resonance sensor in a first resonance mode and in a second resonance mode in response to receiving the light of the given wavelength. The first and second resonance modes have different polarizations.

In another aspect, the providing the plasmon waveguide resonance sensor comprises selecting at least one parameter, the at least one parameter comprising: a thickness of a dielectric layer of the plasmon waveguide resonance sensor; a thickness of a metallic layer of the plasmon waveguide resonance sensor; and the given wavelength.

In another aspect, the selecting comprises applying a genetic algorithm to optimize the at least one parameter.

In another aspect, a surface plasmon resonance assembly for multimode spectroscopy is provided. The assembly includes a surface plasmon resonance sensor configured to provide a first resonance mode for bulk sensing, in response to light of a given wavelength; a dielectric grating coupled to the surface plasmon resonance sensor for diffracting light, and configured to provide: a second resonance mode for bulk sensing, in response to light of the given wavelength; and a third resonance mode for surface sensing, in response to light of the given wavelength. The first, second, and third resonance modes are associated with at least two different polarizations.

In another aspect, the first resonance mode is a transverse magnetic mode.

In another aspect, the second resonance mode is a transverse magnetic mode.

In another aspect, the third resonance mode is a transverse electric mode.

In another aspect, the dielectric grating comprises silica nanowires.

In another aspect, a method of performing multimode spectroscopy is provided. The method includes providing a surface plasmon resonance assembly comprising a surface plasmon resonance sensor coupled to a dielectric grating; providing light of a given wavelength to the assembly; and operating the surface plasmon resonance assembly in a first resonance mode, in a second resonance mode, and in a third resonance mode, in response to receiving the light of the given wavelength. The first, second, and third resonance modes are associated with at least two different polarizations.

In another aspect, the providing the surface plasmon resonance assembly comprises selecting at least one parameter, the at least one parameter comprising: a height of the grating; a period of the grating; and the given wavelength.

In another aspect, the selecting comprises applying a genetic algorithm to optimize the at least one parameter.

In another aspect, a surface plasmon resonance assembly for multimode spectroscopy is provided. The assembly includes: a surface plasmon resonance sensor; a metallic grating coupled to the surface plasmon resonance sensor configured to excite a plurality of resonances modes in the surface plasmon resonance sensor, the resonance modes comprising: a first resonance mode for surface sensing, in response to light of a first wavelength; a second resonance mode for surface sensing, in response to light of the first wavelength; and a third resonance mode for bulk sensing, in response to light of a second wavelength. The first, second, and third resonance modes are associated with at least two different polarizations.

In another aspect, the metallic grating comprises gold nanowires.

In another aspect, a method of performing multimode spectroscopy is provided. The method includes providing a surface plasmon resonance assembly comprising a surface plasmon resonance sensor coupled to a metallic grating; providing light of a first wavelength to the assembly; operating the surface plasmon resonance assembly in a first resonance mode and in a second resonance mode in response to receiving the light of the first wavelength; providing light of a second wavelength to the assembly; and operating the surface plasmon resonance assembly in a third resonance mode in response to receiving the light of the second wavelength. The first, second, and third resonance modes are associated with at least two different polarizations.

In another aspect, the providing the surface plasmon resonance assembly comprises selecting at least one parameter, the at least one parameter comprising: a height of the grating; a period of the grating; the first wavelength; and the second wavelength.

In another aspect, the selecting comprises applying a genetic algorithm to optimize the at least one parameter.

In this respect, before explaining at least one embodiment in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

In the drawings, embodiments are illustrated by way of example. It is to be expressly understood that the description and drawings are only for the purpose of illustration and as an aid to understanding, and are not intended as a definition of the limits.

DETAILED DESCRIPTION

In some embodiments, a plasmon waveguide resonance (PWR) apparatus for multimode spectroscopy at a single wavelength is provided.

In other embodiments, multimode spectroscopy, based on a prism-grating based SPR (PGSPR) sensor is described, which provides spectroscopy in two or more modes, which may depend on various characteristics of the grating. Two examples of PGSPR are described, including a dielectric grating SPR (DGSPR) and a metallic grating SPR (MG-SPR).

Multimode Spectroscopy Using a Plasmon Waveguide Resonance (PWR) Sensor

Parameters which can alter the SPR wave characteristics may be categorized in two general categories: (1) surface effects which include thickness and refractive index of adlayer (2) bulk effects which contain variations in the refractive index of the bulk solution (due to change in buffer concentration or temperature) flowing above the adlayer.

As noted, however, spectroscopy using a single SPR wave cannot distinguish between variations in more than one parameter within the penetration depth.

A conventional SPR sensor may not be able to differentiate between adlayer and bulk solution properties, as the conventional SPR sensor only relies on a single mode spectroscopy.

Other apparatuses for multimode spectroscopy have generally required multiple lasers (e.g., of multiple wavelengths) in order to operate in multiple modes.

Biosensors that can be utilized for multimode spectroscopy may be desirable, for example, to remove the effect of background index variations from the variations in the associated adlayer without the need to have multiple lasers to operate in multiple modes.

Figure 1:
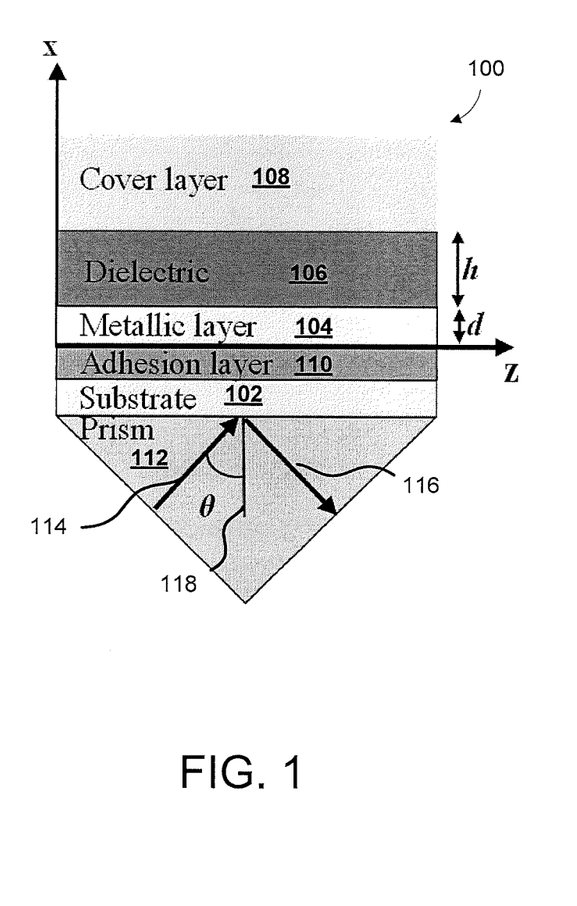
FIG. 1 is a schematic diagram of a PWR sensor, according to some embodiments.

Referring to FIG. 1, a PWR sensor 100 is provided, according to some embodiments. The PWR sensor 100 is adapted for multimode spectroscopy where, in response to light of a given wavelength, the PWR sensor 100 provides a first resonance mode for bulk sensing and a second resonance mode for surface sensing.

The PWR sensor 100 may be configured to provide resonance modes in both transverse electric (TE) and transverse magnetic (TM) polarizations, and there may be one or more resonance modes provided in each of TE and TM polarizations. For example, there may be one or more resonance mode provided for bulk sensing, which may be, e.g., TM resonance modes. There may also be one or more resonance modes provided for surface sensing, which may be, e.g., TE resonance modes.

In some embodiments, the various resonance modes (e.g., for both bulk sensing and surface sensing) may be produced in response to the light received at a single given wavelength, without requiring the need for multiple sources operating at different wavelengths.

Accordingly, the PWR sensor 100 can be configured to operate in the various resonance modes for use in various spectroscopy applications, such as identifying various attributes and/or properties (e.g., mechanical, physical, chemical) of an analyte, for example, measuring the interaction of the analyte with electromagnetic radiation having different polarizations and directionality.

The PWR sensor 100 may be comprised of a substrate 102, a metallic layer 104, and a dielectric layer 106 disposed proximate to the metallic layer 104.

In some embodiments, one or both of the metallic layer 104 and the dielectric layer 106 are provided in the form of gratings, having various geometries and/or physical characteristics, such as a height, a period, and adaptations for various given wavelengths. The gratings may be configured such that one or more additional resonance modes are provided through the use of the grating, the grating splitting the incoming light into several diffraction orders. For example, a metallic grating or a dielectric grating may have parameters selected such that different waves at various resonance modes are produced. Properties of the waves and their interaction with an analyte may be measured so that, for example, various properties of an adlayer can be determined.

The PWR sensor 100 may be used in a method for performing spectroscopy across multiple modes, wherein the method includes steps of providing a surface plasmon assembly including a surface plasmon resonance sensor coupled to a dielectric grating, providing light of a given wavelength to the assembly and operating the surface plasmon assembly in various resonance modes, such as a first resonance mode and a second resonance mode, in response to receiving the light of a given wavelength.

Configuring the PWR sensor 100 for operation may include steps of selecting and/or varying various aspects and/or parameters of the PWR sensor 100, including the thickness of the dielectric layer 106, the thickness of the metallic layer 104, the particular wavelength being used in relation to the PWR sensor 100, etc. The parameters may be selected, for example, through the application of a genetic algorithm to optimize one or more parameters. In some embodiments, an evolutionary computer design program may be used to utilize genetic algorithm principles, such as a genetic representation of the solution domain and an iteratively applied fitness function to evaluate the solution domain. For example, the thickness of layers 104 and 106 and the wavelength may each be tuned using the genetic algorithm.

The PWR sensor 100 may also be incorporated into various types of devices and/or assemblies, such as spectrometers, downhole testing tools, non-destructive testing tools, industrial manufacturing tools, analytical chemistry tools, biological assay testing tools, bench-top tools, laboratory tools, production-line tools, etc.

In performing multimode spectroscopy, the device and/or assembly may be provided light of a first wavelength, operated in a first resonance mode and a second resonance mode in response to receiving the light of the first wavelength, provided light of a second wavelength and operated in a third resonance mode in response to receiving the light of the second wavelength.

The PWR sensor 100 of FIG. 1 is in the Kretschmann configuration, in which incident light 114 is directed on the substrate through a prism 112 and the reflected light 116 intensity is measured as a function of the angle of incident 118.

Optionally, the PWR sensor 100 may further comprise an adhesion layer 110 and/or a cover layer 108. The adhesion layer 110 may be selected to increase adhesion between the metallic layer 104 and the substrate 102.

While some materials are identified within this description, it should be understood that various components, including the substrate 102, the prism 112, the dielectric layer 106, the metallic layer 104 may be made of various suitable materials, as would be understood by a skilled person in the art. For example, the substrate 102 may be BK7 glass, the adhesion layer 110 may be titanium, the metallic layer 104 may be gold (e.g., arranged as gold nanowires), and the dielectric may be silica (e.g., arranged as silica nanowires).

Depending on the embodiment, it will understood that there may be more or less layers, and each layer may be configured in various arrangements.

In general, PWR sensors can been categorized in two different types (a) the dip type which has tens of nanometers of metal with a relatively low imaginary permittivity, and (b) the peak type with a thinner metallic layer (a few nanometers) with relatively large imaginary permittivity. The PWR sensors 100 may be organized as a dip type, or as a peak type.

In other embodiments, other coupling mechanisms, such as Otto configuration, may also be utilized; the invention is not limited only to the Kretschmann configuration.

A contribution of some embodiments is a PWR sensor 100, with dual TE and TM characteristics that can be used for multimode spectroscopy operations.

The PWR sensor 100 may provide self-referenced spectroscopy using both TE and TM polarizations. The role of the metallic layer 104 is to excite the dielectric waveguide modes (TE and TM) under certain conditions.

The large probing depth of the TM polarized light in the PWR sensor 100 may be preferable for bulk refractive index sensing and detecting large biomaterials such as bacteria, or temperature variations, among others.

The small probing depth of the TE polarized light may be preferable for surface sensing. The TE mode is localized at the dielectric/water interface which may make it suitable for thin film measurement.

In comparison with a typical SPR sensor, a PWR sensor 100 may have:
  a smaller limit of detection (TM: 55 ng/ml, TE: 9 ng/ml) than the SPR sensor (TM: 63 ng/ml, no TE mode); and
  a better resolution (TM: $5\times10^{-7}$ RIU, TE: $1.4\times10^{-6}$ RIU) than the SPR sensor (TM: $3\times10^{-6}$ RIU, no TE mode).

The PWR sensor 100 may potentially also be less sensitive to temperature fluctuations than a conventional SPR sensor, which may be due to the fact that the PWR sensor 100 contains a dielectric layer which has small thermal conductivity. To illustrate, a conventional SPR sensor may have the metal layer in direct contact with the fluid, while the PWR sensor 100 has a dielectric spacer between the metal and the fluid.

Furthermore, the dielectric layer thickness adds another degree of freedom which can be used to obtain a compromise between the resonance sharpness and the sensitivity and this can further improve the dynamic range.

In some further embodiments, the performance of the PWR sensor may be optimized in various ways, for example, by using a genetic algorithm.

Operation of the PWR Sensor

Figure 2:
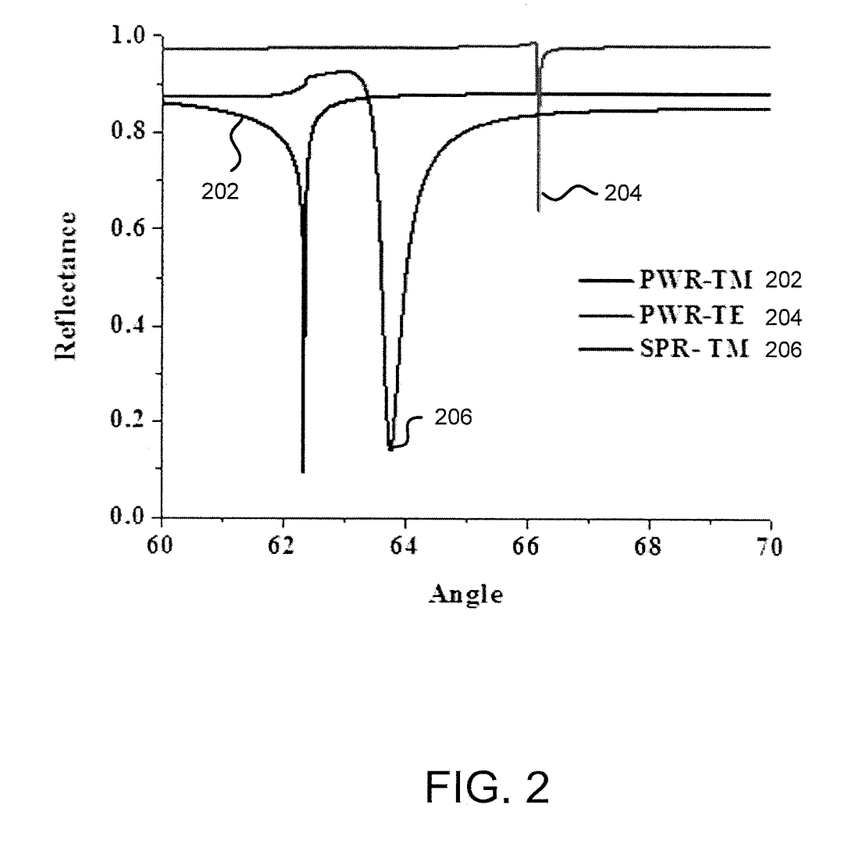
FIG. 2 shows the calculated reflectance spectrum for both an optimized PWR sensor and an optimized SPR sensor, in both TM and TE polarizations, according to some embodiments.

The PWR sensor has two or more distinctive resonance modes at each polarization (as indicated in FIG. 2) which may react to surface and bulk effects differently. For example, a light of a given wavelength may be provided to the PWR sensor 100, which, in response to the light, may provide the different resonance modes. Depending on the particular configuration and/or selection of parameters of the PWR sensor 100, the characteristics of the different resonance modes, and/or the number of different resonance modes may vary.

For example, the PWR sensor 100 may be configured to provide a first resonance mode and a second resonance mode, wherein the first resonance mode is adapted for bulk sensing and the second resonance mode may be adapted for surface sensing. The resonance modes may be, for example, TM and TE modes, respectively.

The TM mode(s) may have a large penetration depth into the fluid (as indicated by the line 202 in FIG. 2) which may be suitable to probe variations in bulk refractive index.

On the other hand, the TE mode(s) may be found to be mostly confined in the top dielectric layer (as indicated by the red line in FIG. 2) where its small penetration depth (up to 300 nm) may be potentially sensitive to the refractive index variations at the dielectric/water interface. Therefore, changes in the bulk refractive index and/or surface binding may lead to different shifts of the TM and TE resonance angles ($\Delta\theta_{TM}$ and $\Delta\theta_{TE}$ respectively).

As indicated by FIG. 2, the TE and TM modes using the PWR sensor are shown to have sharper resonance peaks (see, for example, resonance peaks as indicated on lines 202 and 204).

A potential advantage is that due to the sharp resonance peaks of the modes in the PWR sensor 100, fewer pixels may be required to determine the resonance angle compared to a conventional SPR sensor (as depicted at line 206), providing a larger dynamic range for the PWR sensor 100.

Figure 3:
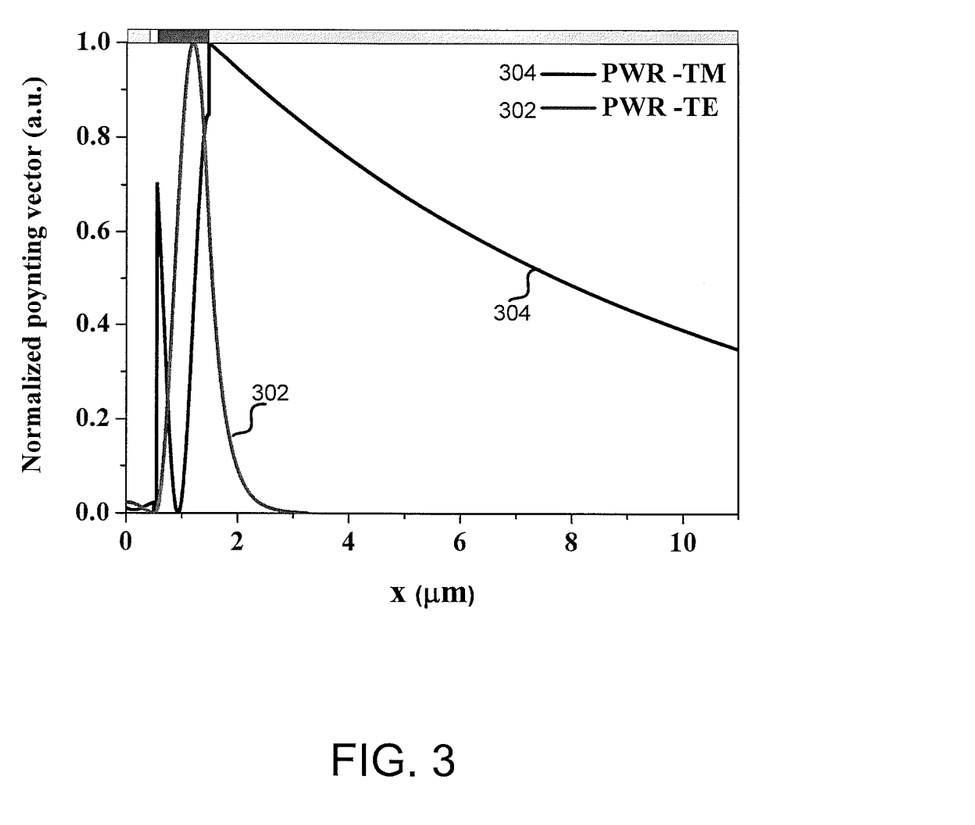
FIG. 3 is a sample graph of the normalized spatial distribution of the power density (Poynting vectors) along the propagation direction (z) as a function of the vertical direction (x).

FIG. 3 provides a sample graph of the normalized spatial distribution of the power density (Poynting vectors) propagation direction (z) as a function of the vertical direction (x), with the line 302 indicating the vector for the TM mode, and the line 304 indicating the vector for the TE mode.

Assuming that the resonance angle shifts are linearly dependent to the surface and bulk effects, the shifts in both polarizations are given by:

$$\Delta\theta = SF_{TM}^{bulk}\Delta n_B + SF_{TM}^{surf}\Delta d_a, \text{ and}$$

$$\Delta\theta_{TE} = SF_{TE}^{bulk}\Delta n_B + SF_{TE}^{surf}\Delta d_a,$$

where $SF_{TM}^{bulk}$ and $SF_{TE}^{surf}$ are the bulk sensitivity factors in degree/refractive index unit (RIU) for TM and TE polarizations, respectively $SF_{TM}^{surf}$ and $SF_{TE}^{surf}$ are surface sensitivity factors in degree/nanometer for the TM and TE polarizations, respectively.

The values of $d_a$ and $n_b$ are the adlayer thickness and bulk refractive index, respectively. Assuming that the sensitivity factors are known (calculated from simulation or measured during a calibration process), differentiating between both unknown parameters ($d_a$ and $n_b$) may be possible using the following equations:

$$\Delta n_B = \frac{SF_{TM}^{bulk} \times \Delta\theta_{TE} - SF_{TE}^{bulk} \times \Delta\theta_{TM}}{SF_{TM}^{bulk} \times SF_{TE}^{surf} - SF_{TM}^{surf} \times SF_{TE}^{bulk}} \text{ and}$$

$$\Delta d_a = \frac{SF_{TE}^{surf} \times \Delta\theta_{TM} - SF_{TM}^{surf} \times \Delta\theta_{TE}}{SF_{TM}^{bulk} \times SF_{TE}^{surf} - SF_{TM}^{surf} \times SF_{TE}^{bulk}},$$

Therefore, by measuring the resonance angles of both polarizations the two unknown variables can be separately determined.

The PWR sensor 100 has a TE resonance mode along with the TM resonance (which is the only resonance mode in the SPR sensors). The TM resonance of the PWR sensor 100 may have a smaller resolution than the TM mode of the SPR sensor. Therefore, the PWR sensor 100 may have a better overall performance than the SPR both in terms of the resolution and the number of the resonance modes. The second mode of the PWR sensor 100 may be used as a reference to improve the reliability of the measurements.

Selection and Optimization

To optimize the PWR sensor, a figure of merit (FoM) may be defined based on the combined sensitivity factor (CSF) to improve the (limits of detection) LOD. The CSF can be written for surface and bulk sensing applications as the following:

$$CSF_{bulk} = SF_{bulk} \times SM = \frac{\partial \theta_{res}}{\partial n_B} \times \frac{R_{max} - R_{min}}{FWHM}, \text{ and}$$

$$CSF_{surf} = SF_{sur} \times SM = \frac{\partial \theta_{res}}{\partial d_a} \times \frac{R_{max} - R_{min}}{FWHM},$$

where $CSF_{bulk}$ and $CSF_{surf}$ are the CSF defined for bulk and surface sensing applications. In the PWR sensor, the TM mode is chosen to monitor bulk effects due to its large penetration depth into the fluid so we include $CSF_{bulk}^{TM}$ in the FoM. The TE mode performs better for surface sensing and therefore $CSF_{surf}^{TE}$ should be considered in the FoM. Thus the FoM is defined as the following function:

$$FoM = CSF_{bulk}^{TM} \times CSF_{surf}^{TE}.$$

A genetic algorithm may be adopted to select various parameters (e.g., optimize) the PWR and SPR sensors by determining the wavelength of operation and layer thicknesses which maximizes the FoM.

Potential Applications

The following is a list of potential applications for some embodiments. The list is a non-limiting list of examples that are provided solely for illustrative purposes:

Single Wavelength Multimode Spectroscopy:

The PWR sensors, along with the DGSPR sensors, may be configured for single wavelength multimode spectroscopy, which may be potentially advantageous as the dispersion properties of the analyte and the buffer solution a priori are not necessary to decouple the quantities of interest, as the multimode measurements are all at the same wavelength. In contrast, the MGSPR performs three measurements at two different wavelengths and therefore the material properties at different wavelength should be known.

Refractive Index Sensor:

PWR sensor can be used as a refractive index sensor for precise measurements of liquid concentration due to the small resolution (RIU) of each resonance mode. One polarization can be used as the sensing channel while the second polarization can be used to improve the reliability of the measurement.

Self Referenced Thin Film Investigation:

The TE mode can be used for thin film (biomolecular layer) measurement while the TM mode can be utilized to remove the background index variations from the TE signal.

Nanoparticle Characterization in Real Time:

By immobilizing nanoparticles (NPs) on the top dielectric layer surface, the affinity of the nanoparticles to the molecular binding can be studied in real time using the PWR sensor with both resonance modes. Here, the TE mode can be used to detect the molecular binding to NP surface while the TM mode can remove the background, index variations. The strength of the nanoparticles attachment to specific dielectrics (e.g. Silica) can also be studied using the PWR sensor.

Gas Sensing:

By immobilizing nanoparticles which are sensitive to specific gas molecules (e.g. Pd nanoparticles for detecting Hydrogen molecules), the change in nanoparticle permittivity values due to the presence of specific gas in the environment can be detected by the TE polarization while the TM polarization can be utilized to detect the temperature variations. Another scheme which does not need nanoparticles for gas sensing is to use the transducer chemical coating on the top dielectric layer, which can absorb specific molecules (e.g. ZnO for ethanol sensing).

Surface Imaging:

The difference in the penetration depth of each resonance mode (up to 300 nm for TE polarization and 9 um for TM polarization) in the PWR sensor can be used for imaging application in which each mode can be used to acquire image from specific depth of the attached layers. By using a thick dielectric layer or stack of dielectric layers, more than one resonance for each polarization can be obtained. Therefore by optimizing layer thicknesses, increasing the number of resonance modes each with different penetration depth into the fluid is possible.

Multimode Spectroscopy Using a PGSPR Sensor

In some embodiments, a dielectric or a metallic grating may be coupled with an SPR sensor to enable the excitement of two or more resonance modes rather than one resonance mode in the SPR sensor. As illustrative, non-limiting examples, two embodiments are described below which can be used to effect spectroscopy with two or more independent modes.

The first platform is comprised of a dielectric grating coupled with a conventional SPR sensor. In this platform, the polarization diversity enables dual polarization spectroscopy at single wavelength which provides two or more resonance modes each optimized to have high sensitivity to a particular measurand.

The second platform is comprised of a metallic grating coupled with a conventional SPR sensor. This arrangement may benefit from a higher order mode excitation and dual wavelength spectroscopy.

Each platform is explained in more detail in the following sections.

Dielectric Grating Coupled with an SPR Sensor

Figure 4A:
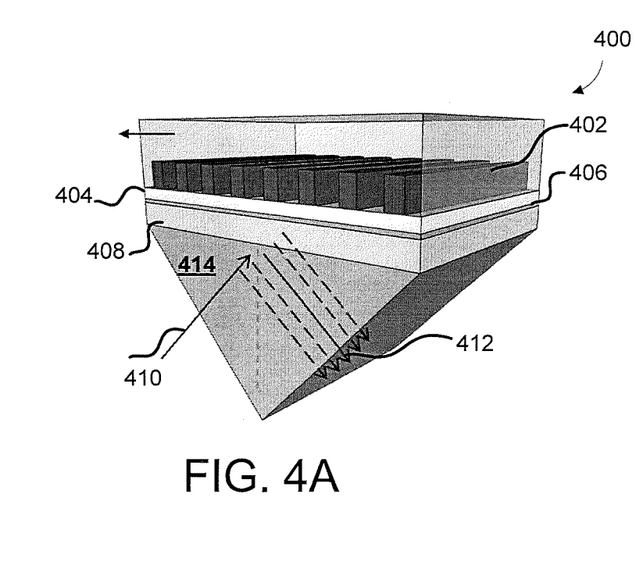
FIG. 4A is a schematic diagram of a dielectric grating based SPR (DGSPR) sensor.
Figure 4B:
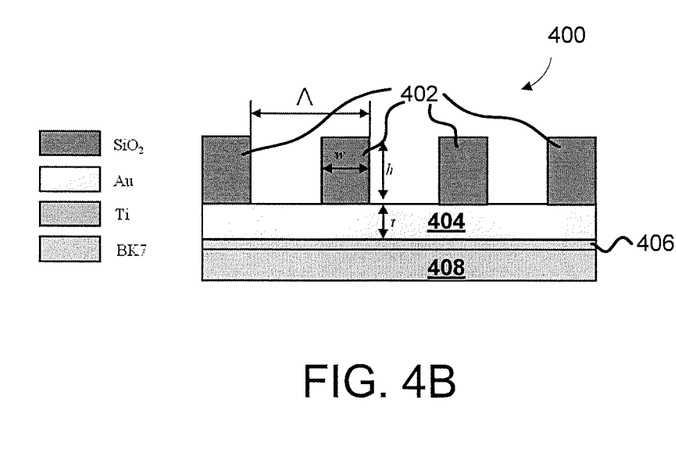
FIG. 4B is a cross-sectional view of the sensor of FIG. 4A, according to some embodiments.

In an embodiment, an SPR sensor is coupled with a dielectric grating, as illustrated at FIGS. 4A and 4B.

FIGS. 4A and 4B illustrate a dielectric grating based SPR (DGSPR) sensor 400. FIG. 4B is a cross-sectional view of the sensor 400 of FIG. 4A. The sensor 400 comprises a dielectric grating 402, a metallic layer 404, an adhering layer 406, and a substrate 408, coupled to a prism 414.

The incident light 410 is diffracted into a series of orders 412, with different values of momentum.

In some embodiments, the dielectric grating 402 is comprised of silica nanowires of a rectangular profile, having a periodicity of Λ, a thickness of h and a filling factor of w/Λ. These factors are design parameters and may be changed depending on the desired output.

A potential advantage of having three mode spectroscopy at two different polarizations is that it can be used to extract more information from the analyte (e.g., adlayer thickness, adlayer refractive index and bulk refractive index).

Each mode may be configured to have a unique property (field profile) and can be used to extract specific information from the analyte under investigation.

The dielectric grating can also be used as a physical filter to separate large cells/molecules from small molecules which is useful for independent study of compound solutions (e.g., blood samples).

Further, by optimizing the thickness of the dielectric grating layer, the number of resonance modes can be increased to more than three.

Dual polarization spectroscopy can be used to study anisotropic materials which have different properties in different directions.

An advantage of this embodiment is that it may provide an SPR biosensor that may overcome the cross sensitivity to the interfering bulk and surface effects.

The metallic layer of the SPR sensor supports an SPR mode which has a transverse magnitude (TM) polarization and the dielectric grating adds two additional waveguide modes: one with TM polarization and the other with TE polarization. Therefore, three different measurements, at two different polarizations can be used to obtain the three desired parameters, i.e. $n_a$, $d_a$, and $n_b$.

Because the proposed sensor operates at a single wavelength, there may be no need to consider the temporal dispersion properties of the analyte or adlayer.

The geometric structure may further be optimized, for example, with the help of a genetic algorithm.

Parameter Selection/Optimization

In this geometry, the momentum of the incident light may be adjusted by diffraction at a rectangular grating to match that of an SPR wave. Assuming that the dispersion properties of the SPR wave is not disturbed by the grating, the momentum conservation between the free space incident light and the SPR wave in the DGSPR sensor may be given by:

$$\pm \sqrt{\frac{\varepsilon_m \varepsilon_d}{\varepsilon_m + \varepsilon_d}} = n_p \sin(\theta_{SPR}) + m\frac{\lambda}{\Lambda},$$

where $\theta_{SPR}$, $\varepsilon_m$, $\varepsilon_d$, $n_p$, $\lambda$, $\Lambda$ and m represent the angle of incident at the resonance, metal permittivity, top dielectric permittivity, prism index of refraction, incident light wavelength, the period of the grating, and the order of diffraction respectively.

The grating diffracts the incident beam into a series of orders, with different values of momentum which can be designed to match the momentum of the surface plasmon.

The sign '+' and sign '−' in the above equation correspond to positive (m>0) and negative (m<0) diffracted orders.

To simultaneously excite multiple modes in this DGSPR sensor, several parameters may be selected, such as, but not limited to: layer thickness, grating periodicity, grating height, filling factor, dielectric (e.g., silica) and/or metallic layer (e.g., gold) thickness, and the wavelength(s) of the incident light.

To optimize the design and to evaluate its performance for biosensing application, a proper figure of merit (FoM) may be defined.

In most of the affinity biosensors, the minimum detectable amount of the quantity to be measured, also called the limit of detection (LoD). In this work, the FoM is defined as the product of CSF corresponding to each mode:

$$FoM = \prod_i CSF, \, i = 1, 2, \ldots$$

To optimize the above-noted parameters, a genetic algorithm (GA) may be used. The GA may be helpful especially when several design parameters should be optimized simultaneously.

In some embodiments, the DGSPR sensor may be optimized with parallelization of the GA implemented on one or more servers, or one or more cloud-computing devices.

In some embodiments, the sensor may be further arranged to increase the number of resonance modes of the DGSPR sensor by adjusting the grating dimensions.

For example, a DGSPR sensor may be modified such that the silica grating in is replaced with an SU8 grating which is an epoxy-based negative photoresist. Then the DGSPR sensor is re-optimized to acquire five resonances at both TM and TE polarizations.

A potential advantage of the DGSPR is its blood cell separation function for blood sensing applications. The microslit arrays of the dielectric grating can physically filter the large blood cells from serum proteins enabling the independent study of large blood cells and small serum proteins using three modes of the DGSPR sensor.

Metallic Grating Coupled with a Conventional SPR Sensor

Figure 5A:
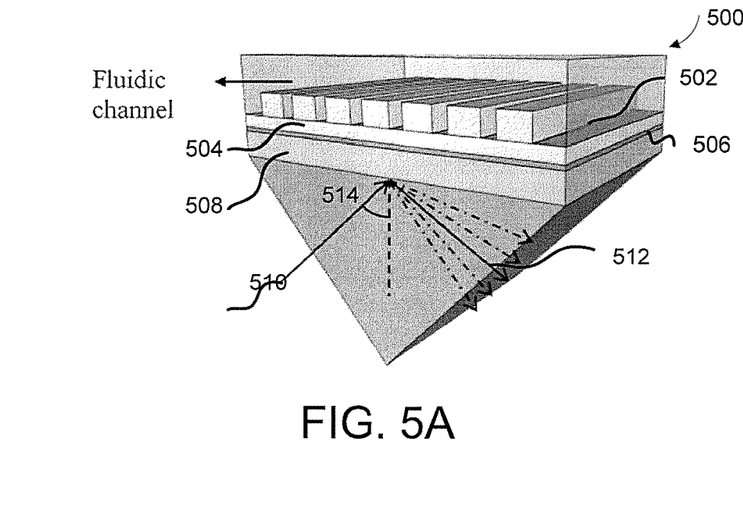
FIG. 5A is a schematic diagram of a metallic grating based SPR (MGSPR) sensor.
Figure 5B:
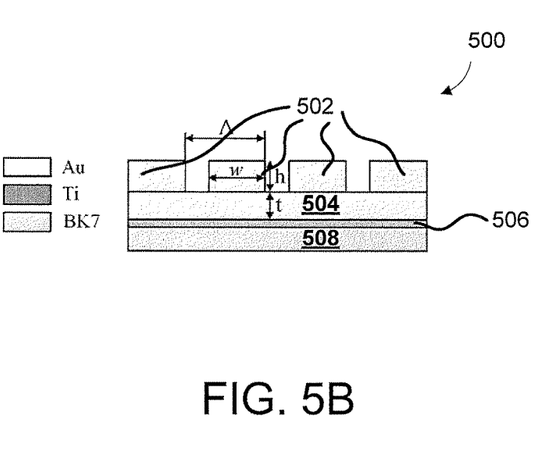
FIG. 5B is a cross-sectional view of the sensor of FIG. 5A, according to some embodiments.

In an embodiment, an SPR sensor is coupled with a metallic grating, as illustrated at FIGS. 5A and 5B.

FIGS. 5A and 5B illustrate a metallic grating based SPR (MGSPR) sensor 500. FIG. 5B is a cross-sectional view of the sensor 500 of FIG. 5A. The sensor 500 comprises a metallic grating 502, a metallic layer 504, an adhering layer 506, and a substrate 508, coupled to a prism 514.

In some embodiments, the metallic grating 502 and the metallic layer 504 may be made of the same materials and may be integral to one another.

In some embodiments, the metallic grating 502 is comprised of elements of a rectangular profile, having a periodicity of Λ, a thickness of h and a filling factor of w/Λ. These factors are design parameters and may be changed depending on the desired output.

A metallic grating may be configured so that three SPR waves at two different wavelengths are excited. In this configuration, the adlayer properties ($d_a$ and $n_a$) can be determined from the bulk index ($n_b$) variations by dual wavelength measurements.

Assuming that the dispersion properties of SPR wave is not disturbed by the grating, the momentum conservation between the free space light and the SPR wave in MGSPR sensor can be expressed by the following equation:

$$\pm\sqrt{\frac{\varepsilon_m \varepsilon_d}{\varepsilon_m + \varepsilon_d}} = n_p \sin(\theta_{SPR}) + m\frac{\lambda}{\Lambda}.$$

A potential use of the MGSPR sensors is to enhance the sensitivity by creating local field enhancement and increasing sensing surface area.

Three mode spectroscopy at two different wavelengths may be useful to extract more information from the analyte (e.g. adlayer thickness, adlayer refractive index and bulk refractive index), relative to spectroscopy at a single wavelength.

Further, the MGSPR may have a higher coupling efficiency to each mode while the DGSPR may have a smaller coupling efficiency to the TE modes.

The MGSPR may also have a larger metallic region as a sensing surface compared to the DGSPR, the MGSPR providing more metallic surface to cover with the target molecules.

Parameter Selection/Optimization

To simultaneously excite multiple SPR waves in a prism-grating based geometry, several parameters may be selected (e.g., adjusted, optimized, configured, chosen), including but not limited to: dielectric/metal layer thickness, grating periodicity, grating height, filling factor, metal (e.g., gold) thickness, and incident wavelength(s).

Variations in the aforementioned parameters may alter the propagation constant of the mode(s).

The optimization of these parameters should be so that each of the excited modes show high sensitivity to the surface or bulk effects. Accordingly, defining a proper figure of merit (FoM) may be important to evaluate a mode's characteristics.

Finding a suitable FoM may be important in making a qualitative analysis on the sensing performance of each mode, and may be found similar to the above sections for the PGSPR.

To optimize the proposed biosensor, a genetic algorithm (GA) is considered among other optimization techniques. GA is an optimization tool that may be especially useful when several design parameters should be optimized simultaneously.

In some embodiments, the MGSPR sensor may be optimized with parallelization of the GA implemented on one or more servers or more cloud-computing devices.

In some embodiments, the sensor may be further arranged to increase the number of resonance modes of the MGSPR sensor by adjusting the grating dimensions and/or frequency.

Potential Applications of Dielectric or Metallic Grating-Based Sensors

The following is a list of potential applications for some embodiments. The list is a non-limiting list of examples that are provided solely for illustrative purposes:

Single Wavelength Multimode Spectroscopy:

The DGSPR sensors, along with the PWR sensors, may be configured for single wavelength multimode dual polarization spectroscopy, which may be potentially advantageous as the dispersion properties of the analyte and the buffer solution are not necessarily decoupled from the quantities of interest. Moreover, MGSPR can be used to perform three measurements at two different wavelengths and polarizations to further decouple the interfering effects associated with any sensing event.

Self Referenced Thin Film Investigation:

Due to the unique field profiles of the grating (dielectric or metallic) based sensor, extracting information from more than three unknown properties (e.g., adlayer thickness, adlayer refractive index, bulk refractive index, temperature, etc.) of an analyte is possible.

Gas Sensing:

By using suitable transducers with high affinity to a specific gas molecule in a periodic configuration as the grating layer, the grating based sensor can be utilized as a gas sensor while the effect of temperature can be removed from the signal by dedicating a mode to sense the temperature fluctuations.

Given the need for qualitative and quantitative analysis of binding kinetics between molecules or biomolecules with nanoparticles (for example, nano-gold particles) embodiments of the PWR, DGSPR, and MGSPR sensors, with their ability to perform multimode and dual polarizations measurements, may be used for such analysis.

Sensor Assemblies

In some embodiments, the apparatuses disclosed herein may be provided in the form of an assembly and/or other device adapted for multimode spectroscopy. For example, sensor systems may also be incorporated into various types of devices and/or assemblies, such as spectrometers, downhole testing tools, non-destructive testing tools, industrial manufacturing tools, analytical chemistry tools, biological assay testing tools, bench-top tools, laboratory tools, production-line tools, etc.

Figure 6:
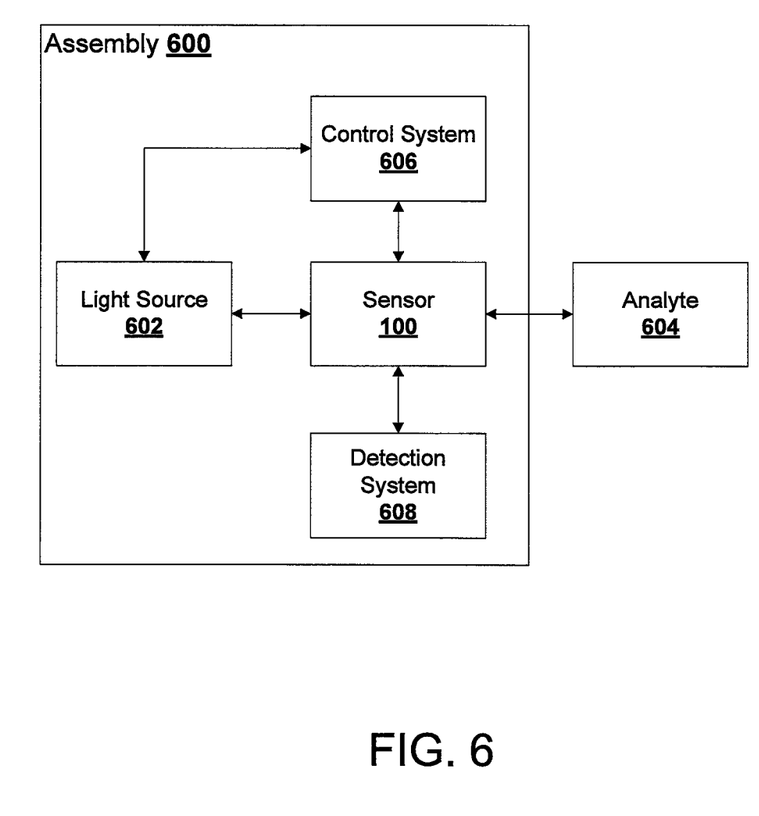
FIG. 6 is a schematic diagram of a sensor assembly, according to some embodiments.

A simplified example is provided at FIG. 6, where an assembly 600 is provided having light source 602, a sensor 100 and an analyte 604. The light source 602 provides light of various wavelengths (e.g., at a first and/or at a second wavelength) to the sensor 100. The assembly 600 may be associated with a control system 606 or detection systems 608. The control system 606 may be configured for controlling various aspects of how the sensor and/or sources operate, and the detection systems 608 may detect various characteristics of the resonance modes and provide one or more outputs, which may be analyzed to determine various characteristics of the analyte.

Methods of Performing Multimode Spectroscopy

Figure 7:
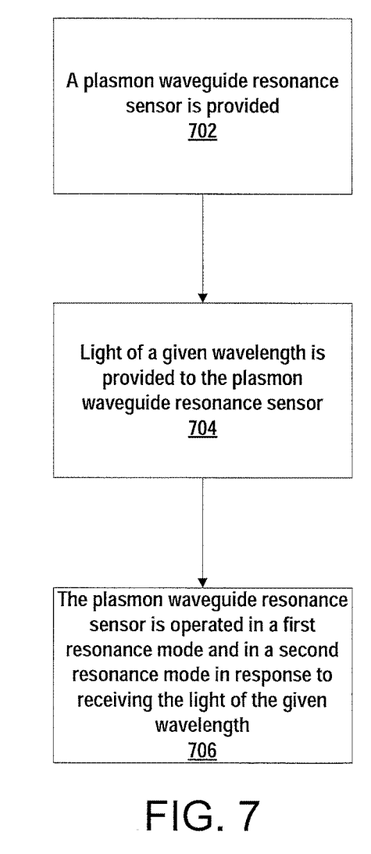
FIG. 7 is a sample workflow diagram for a method of performing multimode spectroscopy using a plasmon waveguide resonance sensor, according to some embodiments.

FIG. 7 is a sample workflow providing some steps in a method of performing multimode spectroscopy with a provided plasmon waveguide resonance sensor, according to some embodiments.

At 702, a plasmon waveguide resonance sensor is provided. Providing the plasmon waveguide resonance sensor may further include selecting at least one parameter, the at least one parameter comprising: a thickness of a dielectric layer of the plasmon waveguide resonance sensor; a thickness of a metallic layer of the plasmon waveguide resonance sensor; and the given wavelength, and the selecting may include applying a genetic algorithm to optimize the at least one parameter.

At 704, light of a given wavelength is provided to the plasmon waveguide resonance sensor.

At 706, the plasmon waveguide resonance sensor is operated in a first resonance mode and in a second resonance mode in response to receiving the light of the given wavelength.

Figure 8:
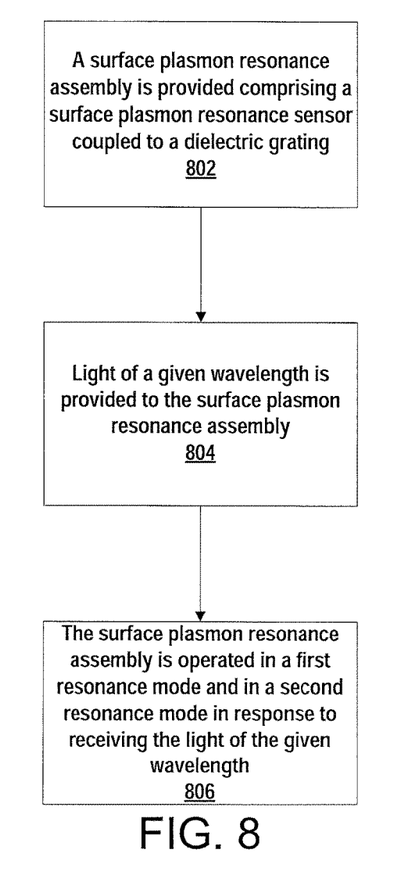
FIG. 8 is another sample workflow diagram for a method of performing multimode spectroscopy using a surface plasmon resonance assembly, according to some embodiments.

FIG. 8 is another sample workflow providing some steps in a method of performing multimode spectroscopy using a surface plasmon resonance assembly, according to some embodiments.

At 802, a surface plasmon resonance assembly comprising a surface plasmon resonance sensor coupled to a dielectric grating is provided. Providing the assembly may further include selecting at least one parameter, the at least one parameter comprising: a height of the grating; a period of the grating; and the given wavelength, and the selecting may include applying a genetic algorithm to optimize the at least one parameter.

At 804, light of a given wavelength is provided to the assembly.

At 806, the assembly is operated in a first resonance mode and in a second resonance mode in response to receiving the light of the given wavelength.

Figure 9:
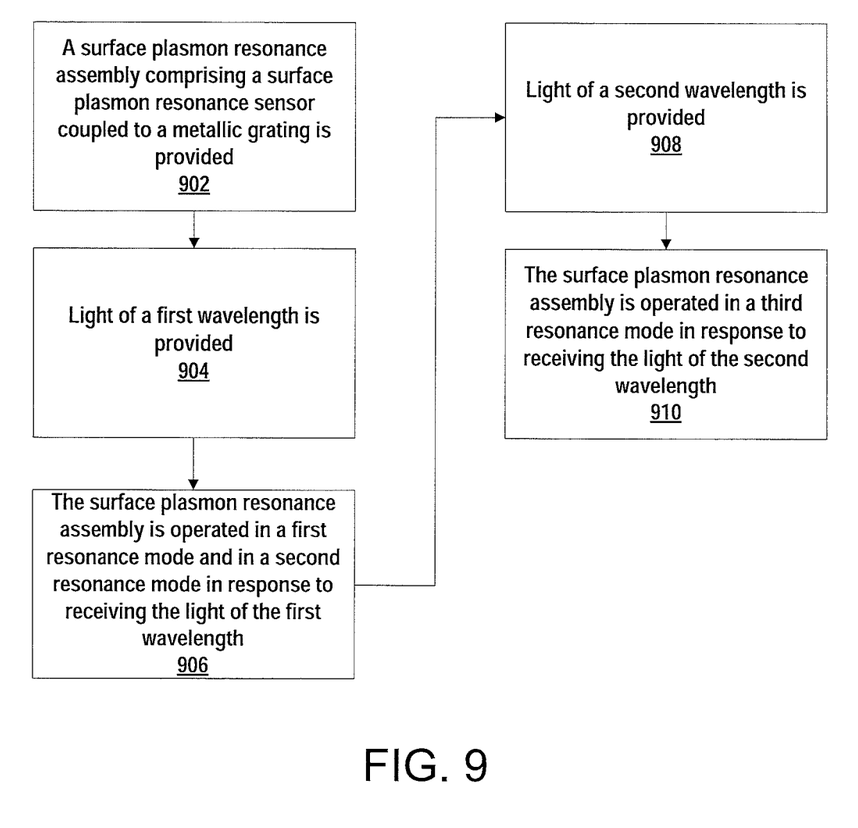
FIG. 9 is another sample workflow diagram for a method of performing multimode spectroscopy using a surface plasmon resonance assembly and light of a first and a second wavelength, according to some embodiments.

FIG. 9 is another sample workflow providing some steps in a method of performing multimode spectroscopy using a surface plasmon resonance assembly and light of a first and a second wavelength, according to some embodiments.

At 902, a surface plasmon resonance assembly comprising a surface plasmon resonance sensor coupled to a metallic grating is provided. Providing the assembly may further include selecting at least one parameter, the at least one parameter comprising: a height of the grating; a period of the grating; the first wavelength; and the second wavelength, and the selecting may include applying a genetic algorithm to optimize the at least one parameter.

At 904, light of a first wavelength is provided to the surface plasmon resonance assembly.

At 906, the surface plasmon resonance assembly is operated in a first resonance mode and in a second resonance mode in response to receiving the light of the first wavelength.

At 908, light of a second wavelength is provided to the surface plasmon resonance assembly.

At 910, the surface plasmon resonance assembly is operated in a third resonance mode in response to receiving the light of the second wavelength.

General

Although the disclosure has been described and illustrated in exemplary forms with a certain degree of particularity, it is noted that the description and illustrations have been made by way of example only. Numerous changes in the details of construction and combination and arrangement of parts and steps may be made. Accordingly, such changes are intended to be included in the invention, the scope of which is defined by the claims.

Except to the extent explicitly stated or inherent within the processes described, including any optional steps or components thereof, no required order, sequence, or combination is intended or implied. As will be understood by those skilled in the relevant arts, with respect to both processes and any systems, devices, etc., described herein, a wide range of variations is possible, and even advantageous, in various circumstances, without departing from the scope, which is to be limited only by the claims.

What is claimed is:

1. A surface plasmon resonance assembly for multimode spectroscopy, the assembly comprising:
    a surface plasmon resonance sensor;
    a metallic grating coupled to the surface plasmon resonance sensor configured to excite a plurality of resonances modes in the surface plasmon resonance sensor, the resonance modes comprising:
        a first resonance mode for surface sensing, in response to light of a first wavelength;
        a second resonance mode for surface sensing, in response to light of the first wavelength; and
        a third resonance mode for bulk sensing, in response to light of a second wavelength;
    wherein the first, second, and third resonance modes are associated with at least two different polarizations.

2. The assembly of claim 1, wherein the metallic grating comprises gold nanowires.

3. The assembly of claim 1, wherein the surface plasmon resonance assembly is configured to optimize at least one parameter, the at least one parameter comprising:
    a height of the grating;
    a period of the grating;
    the first wavelength; and
    the second wavelength.

4. The assembly of claim 3, wherein the optimization of the at least one parameter comprises application of a genetic algorithm to optimize the at least one parameter.

5. A method of performing multimode spectroscopy, the method comprising:
    providing a surface plasmon resonance assembly comprising a surface plasmon resonance sensor coupled to a metallic grating;
    providing light of a first wavelength to the assembly;
    operating the surface plasmon resonance assembly in a first resonance mode and in a second resonance mode in response to receiving the light of the first wavelength;

providing light of a second wavelength to the assembly; and operating the surface plasmon resonance assembly in a third resonance mode in response to receiving the light of the second wavelength, wherein the first, second, and third resonance modes are associated with at least two different polarizations;

wherein the first resonance mode is for surface sensing, in response to light of the first wavelength;

where the second resonance mode is for surface sensing, in response to the light of the first wavelength; and wherein the third resonance mode is for bulk sensing, in response to the light of the second wavelength.

* * * * *